United States Patent
Mito et al.

(10) Patent No.: US 10,386,346 B2
(45) Date of Patent: Aug. 20, 2019

(54) SYSTEM AND METHOD FOR PROCESSING CHROMATOGRAM DATA

(75) Inventors: Yasuhiro Mito, Kyoto (JP); Etsuho Kamata, Kameoka (JP); Hiroshi Miura, Kyoto (JP); Kenichi Mishima, Kameoka (JP); Toshinobu Yanagisawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 822 days.

(21) Appl. No.: 14/342,701

(22) PCT Filed: Aug. 31, 2012

(86) PCT No.: PCT/JP2012/072151
§ 371 (c)(1),
(2), (4) Date: Mar. 21, 2014

(87) PCT Pub. No.: WO2013/035639
PCT Pub. Date: Mar. 14, 2013

(65) Prior Publication Data
US 2014/0257712 A1 Sep. 11, 2014

(30) Foreign Application Priority Data
Sep. 5, 2011 (JP) .................... 2011-193263

(51) Int. Cl.
*G01N 30/86* (2006.01)
*G01N 30/74* (2006.01)

(52) U.S. Cl.
CPC ......... *G01N 30/8675* (2013.01); *G01N 30/74* (2013.01)

(58) Field of Classification Search
CPC ............................ G01N 30/8675; G01N 30/74
(Continued)

(56) References Cited

U.S. PATENT DOCUMENTS

| 6,002,986 A * | 12/1999 | Mito ............... G01N 30/82 702/23 |
| 2007/0273882 A1* | 11/2007 | Smith ............. G01N 21/39 356/437 |
| 2011/0132077 A1* | 6/2011 | Killeen ........... G01N 21/05 73/61.56 |

FOREIGN PATENT DOCUMENTS

| JP | 02-120662 A | 5/1990 |
| JP | 04-184166 A | 7/1992 |

(Continued)

OTHER PUBLICATIONS

JP 2011153966 English Translation.*
(Continued)

*Primary Examiner* — Michael P Nghiem
*Assistant Examiner* — Dacthang P Ngo
(74) *Attorney, Agent, or Firm* — Sughrue Mion, PLLC

(57) ABSTRACT

A data processing system for a chromatograph has an impurity detector including a differential chromatogram creator and a determining section. The differential chromatogram creator calculates a wavelength differential coefficient by differentiating an absorbance spectrum with respect to the wavelength at each point in time of the measurement and creates a differential chromatogram which shows a temporal change in the wavelength differential coefficient. Based on a shape of the thus created differential chromatogram, the determining section determines whether or not a peak of a target component contains an impurity. By this method, whether or not the peak of the target component contains an impurity can be determined with high accuracy, without requiring complex calculations.

10 Claims, 9 Drawing Sheets

(58) Field of Classification Search
USPC .......................................................... 702/25
See application file for complete search history.

(56) References Cited

FOREIGN PATENT DOCUMENTS

| | | |
|---|---|---|
| JP | 2936700 B2 | 8/1999 |
| JP | 2006-177980 A | 7/2006 |
| JP | 2011-153966 A | 8/2011 |

OTHER PUBLICATIONS

Chinese Office Action dated Oct. 10, 2014 in Chinese Patent Office Action 201280042744.9.
Yasuhiro Mito, et al., "Shimadzu Photodiode Array UV-VIS Detector SPD-M6A for HPLC", Shimadzu Hyouron (Shimadzu Review), Jul. 1989, pp. 21-28, vol. 46, No. 1.
Chinese Office Action dated May 22, 2015 in Chinese Patent Application No. 201280042744.9.
Communication dated May 11, 2018 from the Intellectual Property India Patent Office in counterpart India application No. 2277/CHENP/2014.

* cited by examiner

COMPONENT SEPARATION
INSUFFICIENT

COMPONENT SEPARATION
IMPOSSIBLE

SYSTEM AND METHOD FOR PROCESSING CHROMATOGRAM DATA

CROSS REFERENCE TO RELATED APPLICATIONS

This application is a National Stage of International Application No. PCT/JP2012/072151 filed Aug. 31, 2012, claiming priority based on Japanese Patent Application No. 2011-193263 filed Sep. 5, 2011, the contents of all of which are incorporated herein by reference in their entirety.

TECHNICAL FIELD

The present invention relates to a system and method for processing chromatogram data obtained by using a chromatograph, and more specifically, for processing data collected by a spectrometric analysis of a sample containing components separated by a column of a liquid chromatograph (LC) or a sample introduced by a flow injection method.

BACKGROUND ART

In a liquid chromatograph using a photodiode array (PDA) detector or similar multichannel detector, three-dimensional chromatogram data can be obtained with respect to the three dimensions of time, wavelength and absorbance by repeatedly obtaining an absorbance spectrum for an eluate from a column, with the point of injection of the sample into the mobile phase as the base point. FIGS. 13A and 13B are model diagrams showing one example of the three-dimensional chromatogram data. By extracting data obtained at a specific wavelength from the three-dimensional chromatogram data, a wavelength chromatogram showing the relationship between time and absorbance at the specific wavelength can be created. Furthermore, by extracting data obtained at a specific point in time from the three-dimensional chromatogram data, an absorbance spectrum showing the relationship between wavelength and absorbance at that point in time can be created.

A normal procedure for a quantitative analysis of a known kind of target component in the previously described type of liquid chromatograph includes the steps of obtaining a wavelength chromatogram at an absorption wavelength corresponding to the target component and calculating the quantity value by comparing the area (or height) of a peak originating from the target component on that chromatogram with a calibration curve.

There is no problem with such a quantitative determination of a target component if the aforementioned peak on the wavelength chromatogram originates from only the target component. However, a peak is not always composed of a single component (i.e. the target component); it is often the case that a peak contains an unintended impurity. To address this problem, a peak purity determination process has conventionally been performed in order to determine whether the peak in question on the chromatogram originates from only the target component or contains an impurity.

For example, Patent Document 1 discloses a technique for determining the purity of a peak on a chromatogram obtained by a liquid chromatograph using a multichannel detector. In this technique, a degree of matching P of two absorbance spectra $S_0(\lambda)$ and $S(\lambda)$ is calculated by the following equation (1):

$$P = \frac{\sum S_0(\lambda) \cdot S(\lambda)}{\sqrt{\sum S_0^2(\lambda) \cdot \sum S^2(\lambda)}} \quad (1)$$

where $S_0(\lambda)$ is an absorbance spectrum at time $T_0$ corresponding to the peak top of a target peak on a wavelength chromatogram and $S(\lambda)$ is an absorbance spectrum at an arbitrary point in time $T$ before or after $T_0$. The calculated result is graphically shown in such a manner that the target peak is divided into segments along the time axis, each segment painted in a unique color corresponding to the degree of matching P with the peak top, as shown in the examples of FIGS. 14A and 14B, where green represents the degree of matching P of 1.0-0.8, yellow represents 0.8-0.6, and orange represents 0.6 or less. (It should be noted that those colors are represented by different patterns in those figures.)

If the target peak originates from only the target component, the degree of matching P is highest in the vicinity of the peak top and gradually decreases as being apart from the peak top, as shown in FIG. 14A, with the pattern of the segments being approximately symmetrical with respect to the central axis of the peak. By contrast, if an impurity peak exists before or after the peak top of the target peak (i.e. if the target peak contains an impurity), the degree of matching P decreases before or after the peak top. For example, in FIG. 14B, the degree of matching P on the right side of the peak top (in a later range of time) is lower than on the left side. Thus, it is possible to determine that an impurity is likely to be contained within a range around this point in time.

However, in the previously described conventional peak purity determination method, if an impurity peak exists at a position extremely close to the peak top of the target peak, the degree of matching P in a range close to the peak top does not noticeably decrease, so that it is in some cases impossible to correctly detect the presence of the impurity.

As described in Non-Patent Document 1, the previously described peak purity determination method requires setting a noise vector (whose components indicate, for example, the magnitude of a noise at each wavelength) as a parameter for calculating a threshold of the degree of matching P for determining whether or not an impurity peak exists. However, obtaining a noise vector requires complex calculations, such as the sequentially monitoring of the magnitude of the noise over a predetermined range of wavelengths detected by a multichannel detector as well as the calculation of the standard deviation of the temporal change in the noise within that wavelength range.

In the previously described liquid chromatograph, if there are two target components whose quantities need to be determined, and if the retention times of those two components are close to each other, the peaks originating from the target components may be insufficiently separated and overlap each other on the eventually obtained chromatogram, as shown in FIG. 15A. In a conventional process for dealing with such a situation, the two peaks with the tailing and leading portions overlapping each other are vertically divided into front and rear sections as shown in FIG. 15A, the area of each section is calculated, and the quantities of the two components X and Y are respectively computed from the calculated areas. However, the accuracy of the quantity determined in this manner cannot be high since the peak sections obtained by the vertical division do not reflect a true waveform of the elution profile of each component (i.e. the peak waveform to be obtained if the other component is not present).

Another example of the method for separating component peaks is disclosed in Patent Document 2, in which the peak separation is achieved by a computational process other than the vertical division. However, the therein described computational process is rather complex and requires a considerable amount of time. Furthermore, as shown in FIG. 15B if the peaks of the two target components are entirely superposed on each other (with one peak entirely contained in the other), the peaks cannot be separated by any of the previously mentioned techniques, and therefore, it is impossible to determine the quantity of each component.

A flow injection analysis (FIA), which does not use a column (i.e. which includes no component separation), may be used in a quantitative analysis, particularly in the case where the sample to be analyzed contains only a single component. In the FIA method, a predetermined amount of sample is injected in a mobile phase being supplied at a constant flow rate, using an injector for a liquid chromatograph or similar device. The injected sample is carried by the stream of the mobile phase and introduced into a detector. As in the case of an eluate exiting from a column, the concentration of the target component in the mobile phase changes with time, forming a roughly bell-shaped curve. If the sample thus introduced by the FIA method is detected with a multichannel detector, the obtained data will be a three-dimensional data having the three dimensions of time, wavelength and absorbance, which is substantially the same as the previously mentioned data collected by a liquid chromatograph. Accordingly, the term "three-dimensional chromatogram data" as used in the present description should be interpreted as inclusive of the three-dimensional data collected by the FIA method.

BACKGROUND ART DOCUMENT

Patent Document

Patent Document 1: JP-B 2936700
Patent Document 2: JP-A 2006-177980

Non-Patent Document

Non-Patent Document 1: Yasuhiro Mito and Mitsuo Kitaoka, "Shimadzu HPLC-You Foto Daioodo Arei UV-VIS Kenshutsuki SPD-M6A (Shimadzu HPLC Photodiode Array UV-VIS Detector SPD-M6A)", *Shimadzu Hyoron* (*Shimadzu Review*), Vol. 46, No. 1 (July 1989), pp. 21-28

SUMMARY OF THE INVENTION

Problem to be Solved by the Invention

The present invention has been developed to solve the previously described problem, and its first objective is to provide a system and method for processing chromatogram data capable of accurately determining whether or not a target peak contains an impurity, without requiring complex calculations.

The second objective of the present invention is to provide a system and method for processing chromatogram data capable of performing a highly accurate quantitative analysis of two target components, without requiring complex calculations, even if the peaks of the two components overlap each other.

Means for Solving the Problem

To achieve the second objective of the present invention, it is necessary to separate the mutually overlapping peaks of the two target components into individual components. It is evident that any basic technical idea for the peak separation necessary for achieving the second objective can be used for achieving the first objective, by regarding one of the two target components as the true target component and the other component as an unintended impurity.

Thus, the present invention developed for achieving the first and second objectives provides a system for processing three-dimensional chromatogram data collected for a target sample with respect to the three dimensions of time, wavelength and absorbance, including:

a) a differential chromatogram creator for performing data processing, based on the three-dimensional chromatogram data, in such a manner that, for each of the absorbance spectra showing a relationship between the wavelength and the absorbance at respective points in time within an entire or predetermined time range, a wavelength differential coefficient which is a differential coefficient of an absorbance spectrum at a maximum (or minimum) absorption wavelength of a first component is calculated so as to create a differential chromatogram showing a temporal change in the wavelength differential coefficient within the entire or predetermined time range; and b) a chromatogram waveform processor for performing, based on a waveform of the differential chromatogram, either a process of determining whether or not there is one or more other components overlapping the peak of the first component, or a process of determining the quantity of a second component overlapping the peak of the first component.

The three-dimensional chromatogram data is typically a set of data obtained by repeatedly acquiring absorbance spectra by means of a multichannel detector or similar detector from a sample which contains components that have been temporally separated through a column of a chromatograph.

It may also be a set of data similarly acquired from a sample introduced by the FIA method without being separated into components, instead of a sample which has passed through a column.

The detector does not need to be a multichannel type. Any type of detector can be used as long as it can produce a spectrum having a comparatively broad (moderately changing) waveform. Examples include ultraviolet-visible spectrophotometers, infrared spectrophotometers, near-infrared spectrophotometers and fluorescence spectrophotometers, all of which perform wavelength scan to acquire absorbance spectra.

The chromatograph may be either a liquid chromatograph or a gas chromatograph.

The absorbance spectrum shows a relationship between the wavelength of light from a sample and the absorbance at each wavelength. On this absorbance spectrum, one or more maximum (or minimum) absorption wavelengths specific to each substance exist. In many cases, a plurality of maximum (or minimum) absorption wavelengths are found for each substance, although there may be only one wavelength if the measurement is limited to a predetermined range of wavelengths.

There is no specific limitation on the method for obtaining maximum (or minimum) absorption wavelengths of the first component. One method is to allow an operator to directly enter wavelength values, and another possibility is to allow the operator to select a target component and order the system to retrieve corresponding wavelength values from a database. Still another method is to automatically detect a peak from the three-dimensional chromatogram data and compare the peak with a database to determine the maximum (or minimum) absorption wavelength.

In the chromatogram data processing system according to the present invention, a differential chromatogram is created by the differential chromatogram creator as follows: Necessary data are read from a storage section in which, for example, three-dimensional chromatogram data collected for a target sample are stored. For each of the absorbance spectra which show a relationship between the wavelength and the absorbance at respective points in time within the entire or predetermined time range, a wavelength differential coefficient is calculated by differentiating the absorbance with respect to the wavelength at a maximum (or minimum) absorption wavelength of the first component. The wavelength differential coefficients obtained at respective points in time within the entire or predetermined time range are plotted with respect to time to obtain a differential chromatogram which shows the temporal change of the wavelength differential coefficient.

As stated earlier, the maximum (or minimum) absorption wavelengths are specific to each substance. Therefore, the maximum (or minimum) absorption wavelengths of one component normally do not match those of another component. Even if the two components by chance have one common maximum (or minimum) absorption wavelength, each component may possibly have another maximum (or minimum) absorption wavelength that matches none of the maximum (or minimum) absorption wavelengths of the other component. Accordingly, if a peak of a chromatogram is composed of a first component alone and contains no other component, a maximum (or minimum) absorption wavelength of the first component remains being maximum (or minimum) on the absorbance spectra obtained at respective points in time at least within a time range including the peak concerned. Therefore, at this maximum (or minimum) absorption wavelength, the wavelength differential coefficient becomes approximately zero at any point in time and the differential chromatogram becomes flat.

In the case of a peak which originates from the first component and which contains another (second) component, the maximum (or minimum) absorption wavelength of the first component on the absorbance spectra obtained at respective points in time within a time range including the other component changes due to the influence of this component. Therefore, the wavelength differential coefficient at the maximum (or minimum) absorption wavelength does not become zero, and the differential chromatogram becomes a non-flat curve having a convex or concave portion. A smaller amount of second component contained in the peak originating from the first component results in a smaller concave/convex portion appearing on the differential chromatogram, while a larger amount of second component coexisting in the peak leads to a larger concave/convex portion appearing on the differential chromatogram. Thus, the size of the convex/concave portion (i.e. peak) appearing on the differential chromatogram depends on the amount (concentration) of the coexisting second component.

If the number of other coexisting components is one, the size of the peak on the differential chromatogram can be regarded as the amount of that component. Even if whether the number of other coexisting components is single or plural is unknown, it is at least possible to determine whether or not such a component or components are present. Accordingly, based on the waveform of the differential chromatogram, the chromatogram waveform processor determines whether or not there is another component overlapping the peak of the first component or performs quantitative determination of the second component overlapping the peak of the first component.

When the first component is regarded as the target component and the other overlapping component or components as impurities, the task of the chromatogram waveform processor is to determine whether or not an impurity exists with the target component.

For this task, the chromatogram data processing system according to the first mode of the present invention further includes:

c) a wavelength chromatogram creator for creating, based on the three-dimensional chromatogram data, a wavelength chromatogram showing a relationship between the time and the absorbance for an absorption wavelength of the first component, wherein:

the differential chromatogram creator performs data processing, based on the three-dimensional chromatogram data, in such a manner that, for each of the absorbance spectra obtained at respective points in time within a time range including a peak of the target component on the wavelength chromatogram, the wavelength differential coefficient at the maximum (or minimum) absorption wavelength of the first component is calculated so as to create a differential chromatogram showing a temporal change of the wavelength differential coefficient; and the chromatogram waveform processor acts as a determining section for determining, based on the waveform of the differential chromatogram, whether or not an impurity is contained in the peak of the first component which is the target component.

In this system, the "absorption wavelength of the first component" should preferably be selected from the maximum (or minimum) absorption wavelengths of the first component, although a nearby wavelength can also be selected. If the component has a plurality of maximum (or minimum) absorption wavelengths, the wavelength at which the strongest absorption occurs should preferably be selected as the "absorption wavelength of the first component." As for the "maximum (or minimum) absorption wavelength of the first component", if the presence of an impurity peak in the vicinity of the peak top of the target peak is known beforehand, and if the amount of that impurity needs to be determined, it is preferable to select a maximum (or minimum) absorption wavelength at which the differential coefficient of the absorption spectrum with respect to the wavelength has an adequately large value.

The "time range including the peak of the target component" may be obtained by automatically detecting each peak on the wavelength chromatogram and selecting the time range from the start point to the end point of the target peak. It is also possible to allow an operator to manually set the time range having an appropriate width before and after the retention time of the target peak on the wavelength chromatogram.

Even if an impurity peak exists in close proximity to the top of the target peak on the chromatogram (i.e. if their retention times are extremely close to each other), the presence of that impurity will be reflected in the shape of the differential chromatogram created by the differential chromatogram creator. Therefore, the chromatogram data processing system according to the first mode of the present invention can accurately determine whether or not an impurity is contained in the target peak.

Another feature of the aforementioned system is that the differential chromatogram is not created for the entire time range but is limited to the "time range including the peak of the target component", and the determination on the presence or absence of an impurity is performed for that time range. This not only improves the efficiency of determination on the presence of an impurity in the target peak but also further reduces the time required for the determination.

Specifically, in the first mode of the present invention, the determining section can be configured so as to determine whether or not an impurity is contained in the peak of the target component by determining whether or not the differential chromatogram is flat.

When both of the first and second components are regarded as known kinds of target components, the task of the chromatogram waveform processor is to determine the quantities of the two target components.

For this task, the chromatogram data processing system according to the second mode of the present invention is configured as follows:

the differential chromatogram creator performs data processing, based on the three-dimensional chromatogram data, in such a manner that, for each of the absorbance spectra obtained at respective points in time within the entire or predetermined time range, the wavelength differential coefficient at the maximum (or minimum) absorption wavelength of the first component which is a first target component is calculated so as to create a first differential chromatogram showing a temporal change of the wavelength differential coefficient, and the wavelength differential coefficient at the maximum (or minimum) absorption wavelength of the second component which is a second target component is calculated so as to create a second differential chromatogram showing a temporal change of the wavelength differential coefficient; and the chromatogram waveform processor determines the quantity of the second target component based on a peak on the first differential chromatogram at the maximum (or minimum) absorption wavelength of the first target component as well as the quantity of the first target component based on a peak on the second differential chromatogram at the maximum (or minimum) absorption wavelength of the second target component.

As explained earlier, the size of a peak appearing on a differential chromatogram at a maximum (or minimum) absorption wavelength of the first target component reflects the concentration of the second target component. For example, if the concentration of the second target component is zero, the differential chromatogram obtained at the maximum (or minimum) absorption wavelength of the first target component will have a flat shape with no peak on it. Similarly, the size of a peak appearing on a differential chromatogram at a maximum (or minimum) absorption wavelength of the second target component reflects the concentration of the first target component. For example, if the concentration of the first target component is zero, the differential chromatogram at the maximum (or minimum) absorption wavelength of the second target component will have a flat shape with no peak on it. Thus, by focusing on the peak appearing on the differential chromatogram obtained at the maximum (or minimum) absorption wavelength of one target component, it is possible to exclude the influence of that target component and determine the quantity of the other target component.

The maximum (or minimum) absorption wavelength of the second component can be obtained by the method as used for obtaining the maximum (or minimum) absorption wavelength of the first component. That is to say, since the kind of component whose quantity needs to be determined is known beforehand, it is possible to allow an operator to directly enter the wavelength values. Another possibility is to allow the operator to select a target component and order the system to retrieve corresponding wavelength values from a database.

In the chromatogram data processing system according to the second mode of the present invention, the quantitative determination process based on the peak appearing on the differential chromatogram can be performed similarly to a quantitative determination process using a peak appearing on a normal chromatogram. Thus, in the chromatogram data processing system according to the second mode of the present invention, the chromatogram waveform processor may further include:

a calibration information storage for storing, for each of the first and second target components, calibration information showing a relationship between the area or height of a peak appearing on the differential chromatogram and the concentration of the component;

a peak information calculator for calculating the area or height of the peak appearing on each of the first and second differential chromatograms respectively created at the maximum (or minimum) absorption wavelength of the first target component and the maximum (or minimum) absorption wavelength of the second target component based on the three-dimensional chromatogram data corresponding to the target sample; and a quantity calculator for determining the quantity of each target component by comparing the area or height of the peak calculated by the peak information calculator with the calibration information.

The calibration information (e.g. calibration curves) to be stored in the calibration information storage should preferably be prepared by actually analyzing samples each of which contains the first or second target component at a known concentration (i.e. standard samples). This is also similar to the quantitative determination process using a peak appearing on a normal chromatogram.

Creating the previously described differential chromatogram is a very simple process. The calculation of the quantities can also be achieved in an extremely short period of time by performing a quantitative determination process using calibration information prepared beforehand for the differential chromatogram. Accordingly, the present system can quickly determine the quantity of each target component even if the two peaks respectively originating from the two target components overlap each other. Under ideal conditions, the peak on the differential chromatogram has a shape similar to the profile waveform from which the influence of the overlapping component has been excluded, so that the quantity can be determined with high accuracy.

The present invention developed for achieving the first and second objectives also provides a method for processing three-dimensional chromatogram data collected for a target sample with respect to the three dimensions of time, wavelength and absorbance, including:

a) a differential chromatogram creating step, in which data processing is performed, based on the three-dimensional chromatogram data, in such a manner that, for each of the absorbance spectra showing a relationship between the wavelength and the absorbance at respective points in time within an entire or predetermined time range, a wavelength differential coefficient which is a differential coefficient of an absorbance spectrum at a maximum (or minimum) absorption wavelength of a first component is calculated so as to create a differential chromatogram showing a temporal change in the wavelength differential coefficient within the entire or predetermined time range; and b) a chromatogram waveform processing step, in which either a process of determining whether or not there is one or more other components overlapping the peak of the first component, or a process of determining the quantity of a second component overlapping the peak of the first component, is performed based on a waveform of the differential chromatogram.

The first mode of the chromatogram data processing method further includes:

c) a wavelength chromatogram creating step, in which a wavelength chromatogram showing a relationship between the time and the absorbance for an absorption wavelength of the first component is created based on the three-dimensional chromatogram data, wherein:

in the differential chromatogram creating step, based on the three-dimensional chromatogram data, the wavelength differential coefficient at the maximum (or minimum) absorption wavelength of the first component is calculated for each of the absorbance spectra obtained at respective points in time within a time range including a peak of a target component on the wavelength chromatogram, and a differential chromatogram showing a temporal change of the wavelength differential coefficient is created; and in the chromatogram waveform processing step, whether or not an impurity is contained in the peak of the first component which is the target component is determined based on the waveform of the differential chromatogram.

The second mode of the chromatogram data processing method according to the present invention is configured as follows:

In the differential chromatogram creating step, data processing is performed, based on the three-dimensional chromatogram data, in such a manner that, for each of the absorbance spectra obtained at respective points in time within the entire or predetermined time range, the wavelength differential coefficient at the maximum (or minimum) absorption wavelength of the first component which is a first target component is calculated so as to create a first differential chromatogram showing a temporal change of the wavelength differential coefficient, and the wavelength differential coefficient at the maximum (or minimum) absorption wavelength of the second component which is a second target component is calculated so as to create a second differential chromatogram showing a temporal change of the wavelength differential coefficient; and in the chromatogram waveform processing step, the quantity of the second target component is determined based on a peak on the first differential chromatogram at the maximum (or minimum) absorption wavelength of the first target component, and the quantity of the first target component is determined based on a peak on the second differential chromatogram at the maximum (or minimum) absorption wavelength of the second target component.

Effect of the Invention

By the system and method for processing chromatogram data according to the present invention, whether or not an impurity is contained in a target peak can be accurately determined even in the case where the presence of an impurity cannot be detected by the conventional peak purity determination method, as in the case of an impurity peak located in close proximity to the top of the target peak on the chromatogram. Furthermore, unlike the conventional peak purity determination process, it is unnecessary to set a noise vector as a parameter, so that whether or not an impurity is contained in the target peak can be determined by a comparatively simple calculation.

By the system and method for processing chromatogram data according to the present invention, even in the case where the peaks originating from two target components overlap each other or one peak is entirely contained in the other, it is possible to perform high-accuracy quantitative determination based on the profile waveform originating from each target component. The quantitative determination requires only a comparatively simple computing process and can be quickly performed even if an inexpensive personal computer is used.

BRIEF DESCRIPTION OF THE DRAWINGS

FIG. 14A is an example of the peak containing no impurity and FIG. 14B is an example of the peak containing an impurity.

MODE FOR CARRYING OUT THE INVENTION

[Principle of Two-Component Peak Separation and Peak Purity Determination in Present Invention]

Figure 13A:
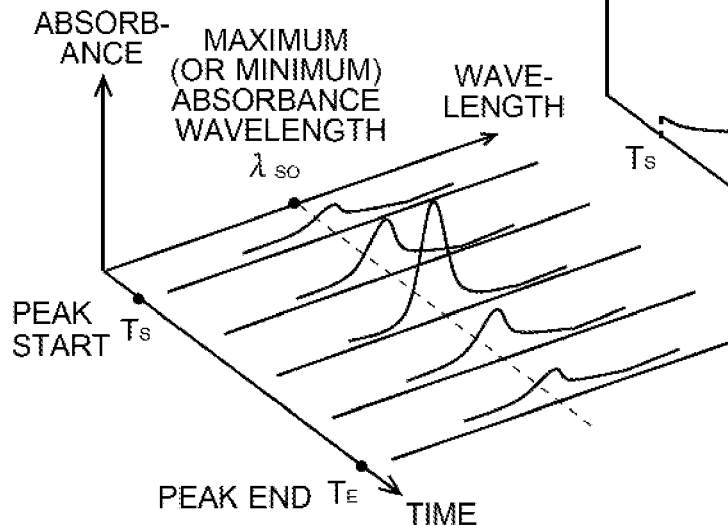
FIGS. 13A and 13B are model diagrams respectively showing a three-dimensional chromatogram data and a maximum (or minimum) absorbance wavelength chromatogram created from the three-dimensional chromatogram data.
Figure 13B:
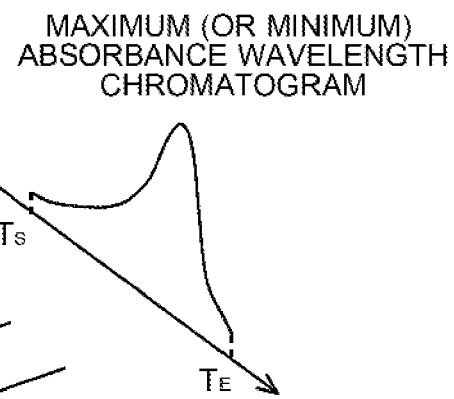
Figure 14A:
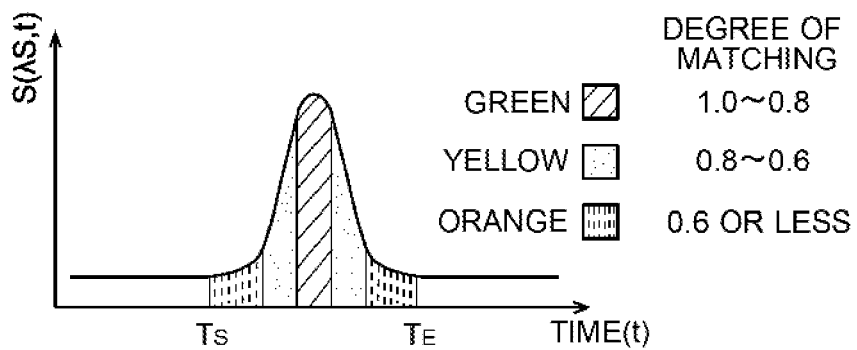
FIGS. 14A and 14B show one example of the method of displaying a result obtained by a conventional peak purity determination process, where
Figure 14B:
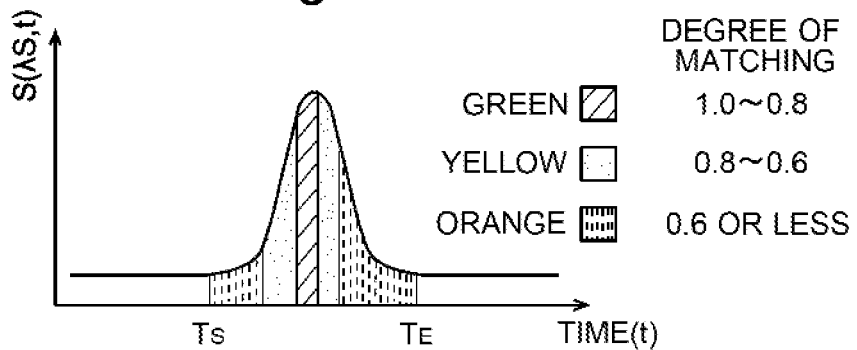

The principle of a two-component peak separation and peak purity determination in the present invention performed on a three-dimensional chromatogram data as shown in FIGS. 13A and 13B is hereinafter described with reference to FIGS. 8-11B.

Figure 8:
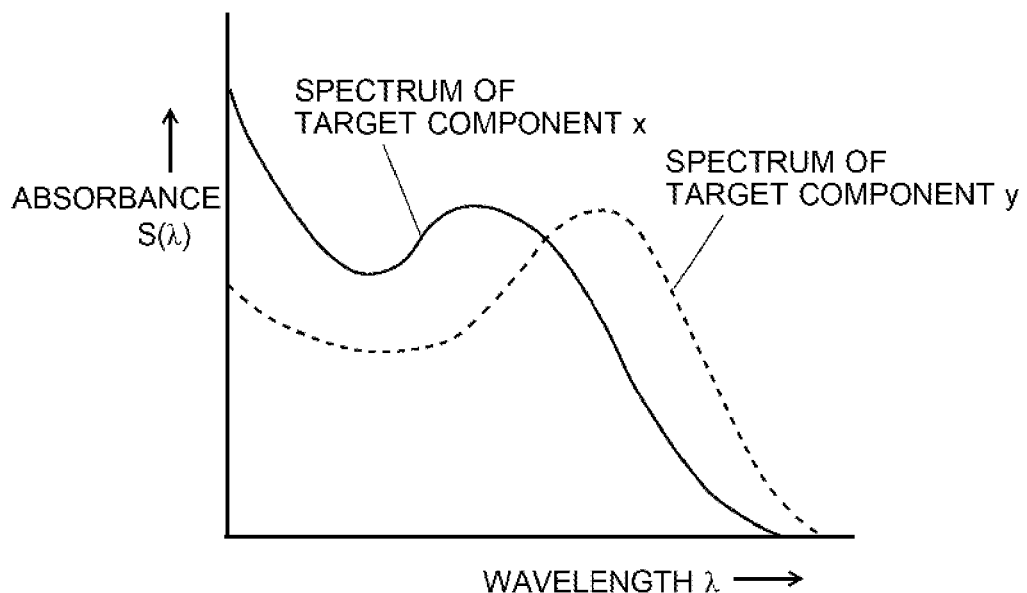
FIG. 8 is a diagram showing one example of the absorbance spectrum for explaining the principle of the two-component peak separation and the peak purity determination in the present invention.

Hereinafter considered is the case where two components x and y are contained in a sample. FIG. 8 shows one example of the absorbance spectra of the components x and y. As shown, different substances normally have different maximum (or minimum) absorption wavelengths, i.e. the wavelength which corresponds to the top (maximum (or minimum) point) of the absorbance peak.

Figure 9:
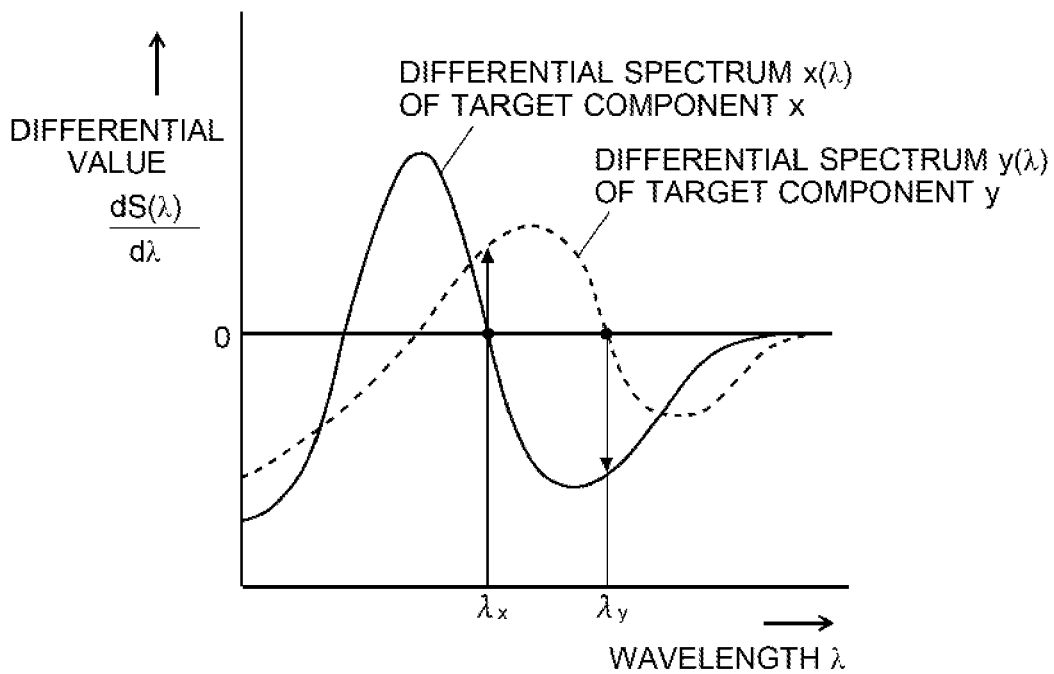
FIG. 9 is a diagram showing a differential spectrum based on the absorbance spectrum shown in FIG. 8.

FIG. 9 is a differential spectrum obtained by differentiating the absorbance spectrum shown in FIG. 8 with respect to the wavelength. The value of the differential coefficient is positive in a phase where the curve ascends with increasing wavelength, negative in a phase where the curve descends with increasing wavelength, and zero at the top or bottom of the absorbance peak. As shown in FIG. 9, the wavelength at which the differential coefficient becomes zero (more specifically, the "zero" which occurs in the phase where the differential coefficient changes from positive to negative values) in the differential spectrum of the component x is denoted by $\lambda x$, while the wavelength at which the differential coefficient becomes zero (similarly, the "zero" which occurs in the phase where the differential coefficient changes from positive to negative values) in the differential spectrum of the component y is denoted by $\lambda y$. That is to say, in the present example, $\lambda x$ is the maximum absorption wavelength of the component x, and $\lambda y$ is the maximum absorption wavelength of the component y.

Figure 10:
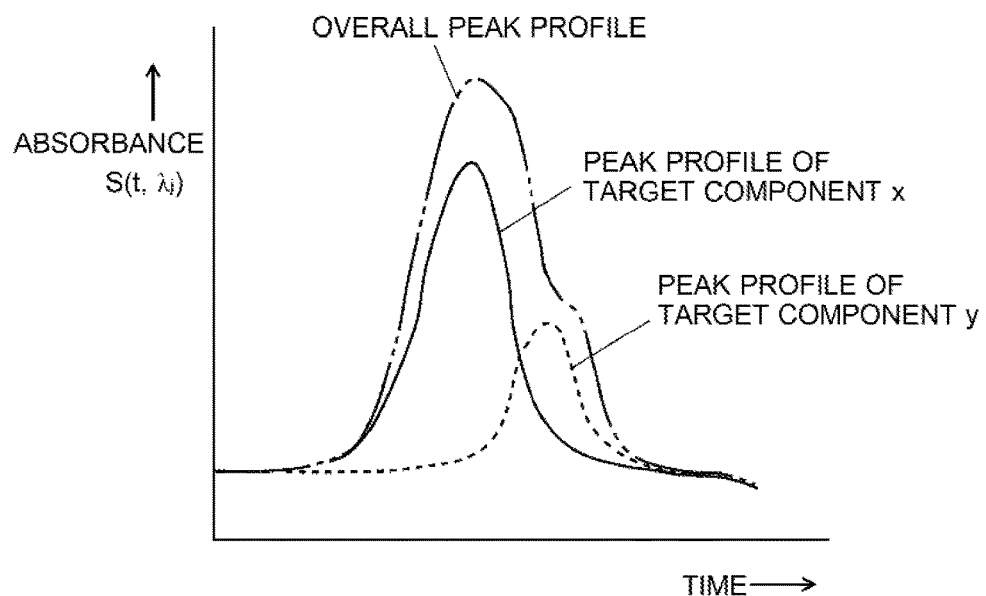
FIG. 10 is a diagram showing a two-component mixture peak on a chromatogram.

FIG. 10 shows one example of the peak profiles of the components x and y on a chromatogram as well as a mixture peak composed of the two peak profiles superposed on each other in an unseparated form. The retention times of the two components x and y are considerably close to each other and it is difficult to predict the individual peak profiles of the components x and y from the mixture peak.

With $x(\lambda)$ denoting the absorbance spectrum of the component x and $a(t)$ denoting its peak profile as well as $y(\lambda)$ denoting the absorbance spectrum of the component y and $b(t)$ denoting its peak profile, a three-dimensional chromatogram $S(t, \lambda)$ of a two-component system in which both components x and y are eluted (with their peaks overlapping each other on a chromatogram) can be expressed by the following equation (2).

$$S(t,\lambda)=a(t)x(\lambda)+b(t)y(\lambda) \quad (2)$$

A partial differentiation of equation (2) with respect to wavelength $\lambda$ gives the following equation (3).

$$\partial S(t,\lambda)/\partial \lambda=a(t)x'(\lambda)+b(t)y'(\lambda) \quad (3)$$

Substituting $\lambda x$ (the wavelength at which the differential coefficient of the differential spectrum of the component x is zero) into equation (3) gives the following equation, since $x'(\lambda x)=0$.

$$\partial S(t,\lambda x)/\partial \lambda=b(t)y'(\lambda x) \quad (4)$$

Similarly, substituting $\lambda y$ (the wavelength at which the differential coefficient of the differential spectrum of the component y is zero) into equation (3) gives the following equation, since $y'(\lambda y)=0$.

$$\partial S(t,\lambda y)/\partial \lambda=a(t)x'(\lambda y) \quad (5)$$

Figure 11A:
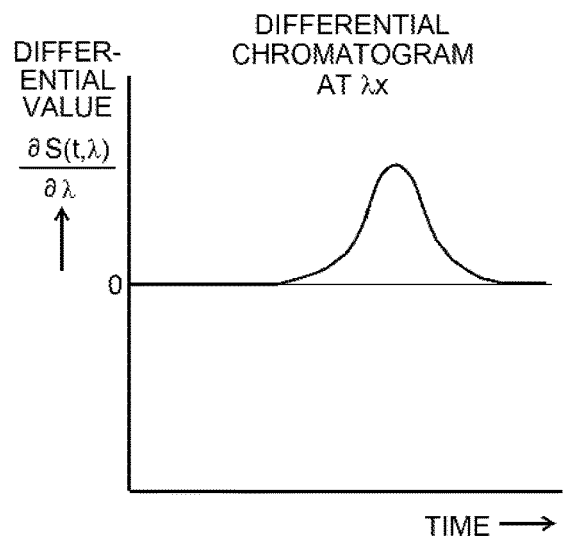
FIGS. 11A and 11B are diagrams showing differential chromatograms based on the differential spectrum shown in FIG. 9.
Figure 11B:
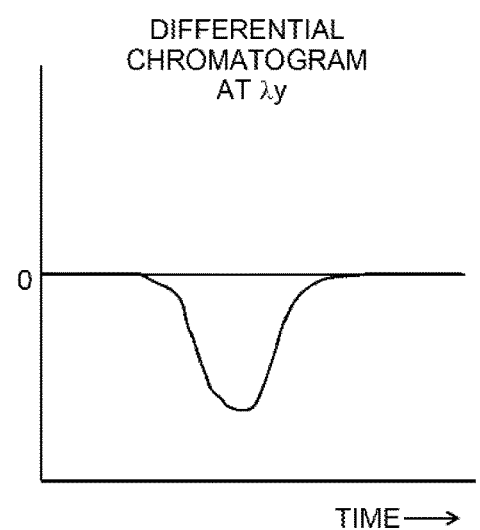

FIG. 11A shows the result of equation (4) plotted with respect to time, and similarly, FIG. 11B shows the result of equation (5) plotted with respect to time. In other words, FIG. 11A is a differential chromatogram at the wavelength $\lambda x$, and FIG. 11B is a differential chromatogram at the wavelength $\lambda y$. As can be understood from equation (4), the differential chromatogram at the wavelength $\lambda x$ has only the peak profile $b(t)$ of the component y appearing on it. Similarly, as can be understood from equation (5), the differential chromatogram at the wavelength $\lambda y$ has only the peak profile $a(t)$ of the component x appearing on it. The areas and/or the heights of those peak profiles $a(t)$ and $b(t)$ depend on the concentrations of the components x and y, respectively. Although the foregoing descriptions relating to FIGS. 9-11B dealt with the case of using the maximum absorption wavelengths $\lambda x$ and $\lambda y$ of the components x and y, it is also possible to use minimum absorption wavelengths of the components x and y in place of the maximum absorption wavelengths.

Thus, even in the situation where both components x and y are eluted, it is possible to separately determine the quantity of only the component y by using a differential spectrum chromatogram in which the differential coefficient with respect to the wavelength of the absorbance spectrum at the maximum (or minimum) absorption wavelength $\lambda x$ of the component x is plotted with respect to time, and similarly, to separately determine the quantity of only the component x by using a differential chromatogram in which the differential coefficient with respect to the wavelength of the absorbance spectrum at the maximum (or minimum) absorption wavelength $\lambda y$ of the component y is plotted with respect to time.

As shown in FIG. 11B, the peak profile of the component x appearing on the differential chromatogram at the maximum (or minimum) absorption wavelength $\lambda y$ becomes a negative peak. Its polarity should be reversed when the quantitative determination is performed.

In FIG. 11A, if no peak has appeared on the differential chromatogram, i.e. if the differential coefficient has remained at zero, it means that the component y did not exist. Thus, based on whether or not a peak is present on a differential chromatogram at the maximum (or minimum) absorption wavelength $\lambda x$ of the component x, it is possible to determine whether or not the component y is overlapping. It is evident that such a simple determination can be made without previous information on the maximum (or minimum) absorption wavelength $\lambda y$ of the component y, and therefore, the component y may be an unknown kind of substance. By expanding this idea, it can be understood that, when the task to be done is to simply determine whether or not a chromatogram peak of one known kind of component contains one or more other components, the number of other components does not need to be one, and those one or more other components can be collectively handled as an impurity.

That is to say, in the case where one or more other components are mixed as impurities in a target component whose three-dimensional chromatogram is expressed as $a(t)x(\lambda)$, the three-dimensional chromatogram $S(t, \lambda)$ of the entire sample can be expressed as follows:

$$S(t,\lambda)=a(t)x(\lambda)+b(t)y(\lambda)+c(t)z(\lambda)+\ldots \quad (6)$$

Partially differentiating this equation with respect to wavelength and substituting into this equation the wavelength λx at which the differential spectrum x'(λ) of the target component x becomes zero gives the following equation (7).

$$\partial S(t,\lambda x)/\partial \lambda = b(t)y'(\lambda x) + c(t)z'(\lambda x) + \ldots \quad (7)$$

This equation is the differential chromatogram at the maximum (or minimum) absorption wavelength λx of the target component x. From this equation, it can be understood that the peak originating from the target component x is eliminated and only the impurity peaks appear on the chromatogram.

Thus, it is possible to determine the presence or absence of impurities in the target component by using the same principle as applied in the previously described case of the two-component peak separation.

[Configuration and Operation of Chromatogram Data Processing System which is First Embodiment of Present Invention]

Figure 1:
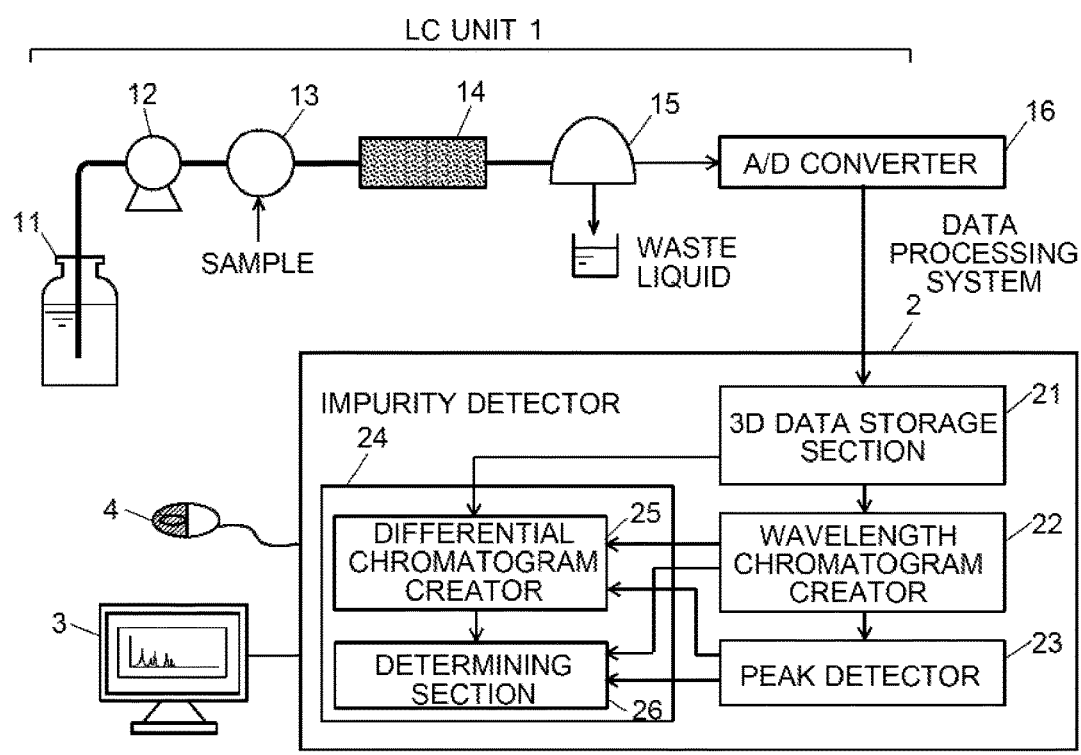
FIG. 1 is a schematic configuration diagram of a liquid chromatograph provided with a chromatogram data processing system which is one embodiment of the present invention.

One embodiment (first embodiment) of the chromatogram data processing system according to the present invention is hereinafter described with reference to FIGS. 1-6. The first embodiment is designed to perform a peak purity determination based on the previously described principle. FIG. 1 is a schematic configuration diagram of a liquid chromatograph system provided with the chromatogram data processing system according to the present embodiment (which is hereinafter simply called the "data processing system").

In the LC unit 1, which is designed for collecting three-dimensional chromatogram data, a liquid-sending pump 12 draws a mobile phase from a mobile-phase container 11 and supplies it to a sample injection unit 13 at a constant flow rate. In the sample injection unit 13, a sample is injected into the mobile phase at a predetermined timing. The sample is carried by the mobile phase into a column 14. While passing through the column 14, the sample is temporally separated into components, which exit from the column 14.

At the exit of the column 14, a PDA detector 15, which is a type of multichannel detector, is provided as a device for detecting the sample components contained in the eluate from the column 14. In the PDA detector 15, a ray of light emitted from a light source (not shown) is cast into the eluate. The light which has passed through the eluate is dispersed into a spectrum of wavelengths, and the intensities of light at those wavelengths are almost simultaneously detected by a PDA linear sensor. The PDA detector 15 repeatedly produces detection signals, which are converted into digital signals by an analogue-to-digital (A/D) converter 16 and sent to the data processing system 2 as three-dimensional chromatogram data.

The data processing system 2 includes a three-dimensional data storage section 21 for storing three-dimensional data produced by the A/D converter 16, a wavelength chromatogram creator 22 for creating, from the three-dimensional chromatogram data, a wavelength chromatogram showing a temporal change of the absorbance at a specific wavelength, a peak detector 23 for detecting a peak in the wavelength chromatogram, and an impurity detector 24 for detecting an impurity contained in a target peak selected by an operator from the detected peaks. In the present embodiment, the wavelength chromatogram creator 22 is configured to create a maximum (or minimum) absorption wavelength chromatogram which shows a temporal change of the absorbance at the maximum (or minimum) absorption wavelength $\lambda_{S0}$ of the target component.

The impurity detector 24 includes, as its functional blocks, a differential chromatogram creator 25 for creating a differential chromatogram based on the three-dimensional chromatogram data and the maximum (or minimum) absorption wavelength $\lambda_{S0}$ of the target component, as well as a determining section 26 for determining the presence or absence of an impurity in the target peak based on the shape of the differential chromatogram. Operations of these functional elements will be described later.

The display unit 3 is used for displaying various kinds of information, such as a maximum (or minimum) absorption wavelength chromatogram, an absorbance spectrum, a differential chromatogram and a result of determination. The operation unit 4 is provided to allow an operator to input or set information or the like necessary for the data processing, such as the maximum (or minimum) absorption wavelength $\lambda_{S0}$ of the target component.

A portion or the entirety of the functions of the data processing system 2 can be implemented by executing a dedicated controlling and processing software program installed in a personal computer or a workstation. The display unit 3 may be a commonly used device, such as a liquid crystal monitor. The operation unit 4 can be constructed using normal equipment of personal computers or workstations, such as a keyboard and a mouse or similar pointing device.

Figure 6:
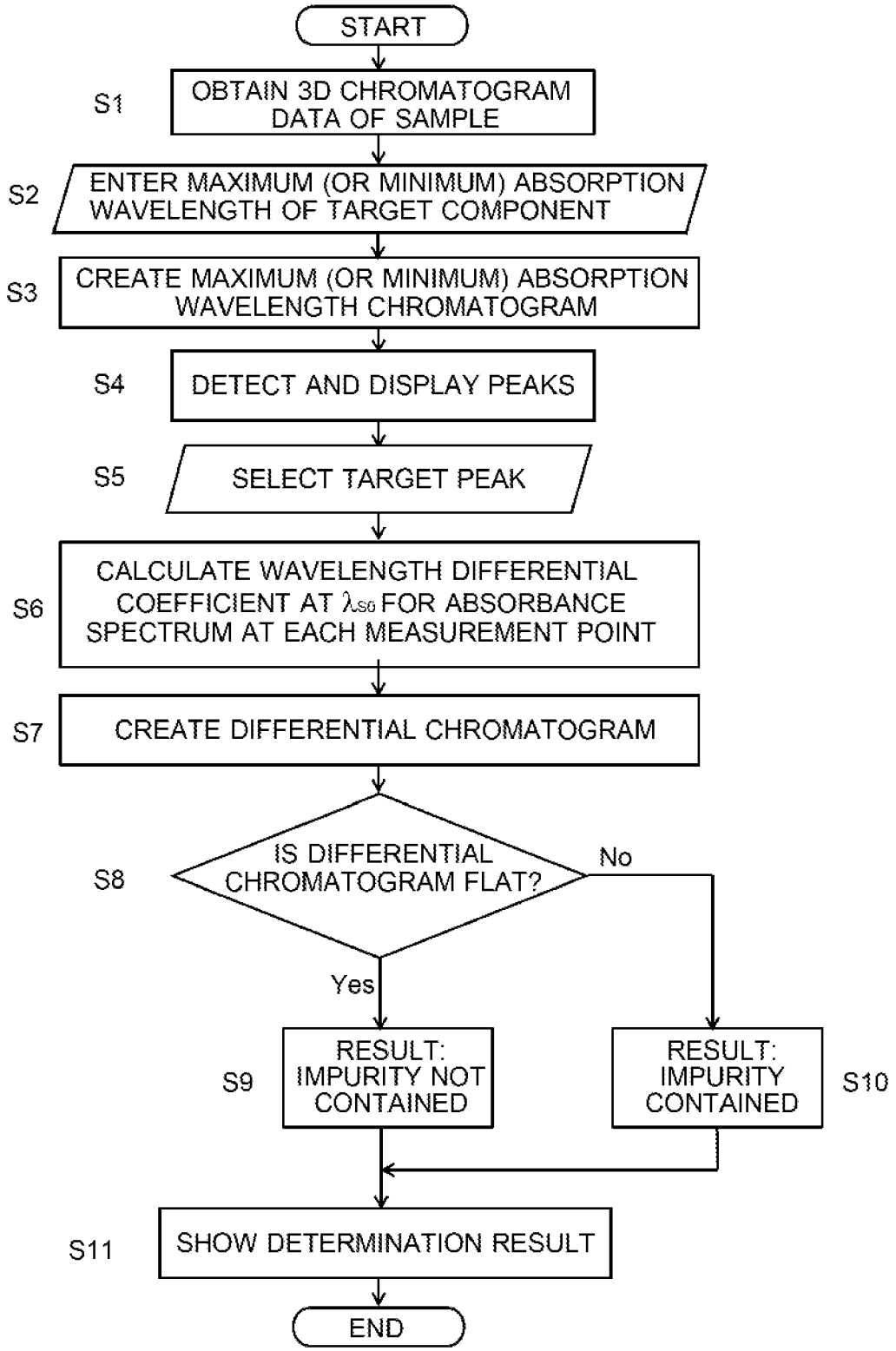
FIG. 6 is a flowchart showing the steps of a peak purity determination process performed by the chromatogram data processing system of the present embodiment.

A data processing operation characteristic of the liquid chromatograph system of the first embodiment is hereinafter described with reference to the flowchart of FIG. 6.

Initially, a chromatographic analysis is performed on a target sample in the LC unit 1, and the thereby produced three-dimensional chromatogram data showing a temporal change of the absorbance spectrum within a predetermined wavelength range (see FIG. 13A) are sent from the PDA detector 15 to the three-dimensional data storage section 21, to be stored in this section 21 (Stop S1).

Next, the operator enters, through the operation unit 4, the value of the maximum (or minimum) absorption wavelength $\lambda_{S0}$ of a target component (e.g. a component whose quantity needs to be determined) contained in the sample (Step S2). In response to this operation, the wavelength chromatogram creator 22 creates a maximum (or minimum) absorption wavelength chromatogram with the horizontal axis indicating the time and the vertical axis indicating the absorbance at the maximum (or minimum) absorption wavelength $\lambda_{S0}$, based on the entered maximum (or minimum) absorption wavelength $\lambda_{S0}$ and the three-dimensional chromatogram data stored in the three-dimensional data storage section 21 (Step S3). FIG. 13B shows one example of the maximum (or minimum) absorption wavelength chromatogram created based on the three-dimensional chromatogram data shown in FIG. 13A.

Figure 2:
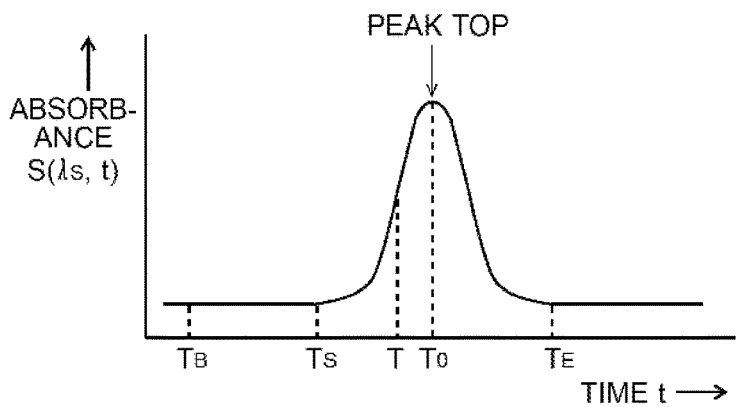
FIG. 2 is a diagram showing one example of the peak of a maximum (or minimum) absorption wavelength chromatogram.

The peak detector 23 sequentially examines the temporal change in the slope of the curve of the maximum (or minimum) absorption wavelength chromatogram created by the wavelength chromatogram creator 22, to detect a peak in such a manner that, as shown in FIG. 2, the point at which the slope reaches a predetermined value in the ascending phase is identified as the start point $T_S$ of the peak, the point at which the slope changes from a positive value through zero to a negative value is identified as the peak top $T_0$, and the point at which the absolute value of the slope reaches a predetermined value in the descending phase is identified as the end point $T_E$ of the peak (Step S4). Although FIG. 2 shows only one peak, a plurality of peaks will normally be detected if the sample contains two or more components. Information on the detected peaks is displayed on a screen of the display unit 3. From the displayed peaks, the operator can select a target peak originating from the target component through the operation unit 4 (Step S5).

Figure 5:
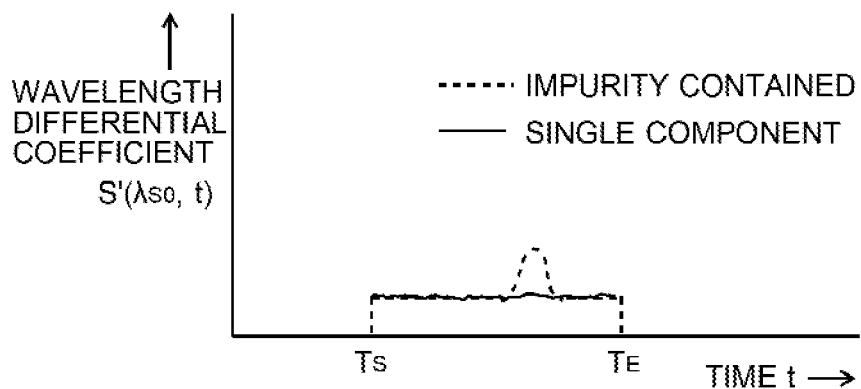
FIG. 5 is a diagram showing one example of the differential chromatogram.

After the target peak is selected, the differential chromatogram creator 25 retrieves, from the three-dimensional data storage section 21, absorbance spectra included in the time range from the start point $T_S$ to the end point $T_E$ of the target peak, calculates a wavelength differential coefficient for each absorbance spectrum by differentiating the absorbance spectrum with respect to wavelength at the maximum (or minimum) absorption wavelength $\lambda_{S0}$ (Step S6), and creates a differential chromatogram with the horizontal axis indicating the time and the vertical axis indicating the calculated wavelength differential coefficient (Step S7). FIG. 5 shows one example of the differential chromatogram.

Based on the differential chromatogram created by the differential chromatogram creator 25, the determining section 26 performs the following process based on the previously described principle to determine whether or not an impurity exists within the time range from the start point $T_S$ to the end point $T_E$ of the target peak.

Figure 4:
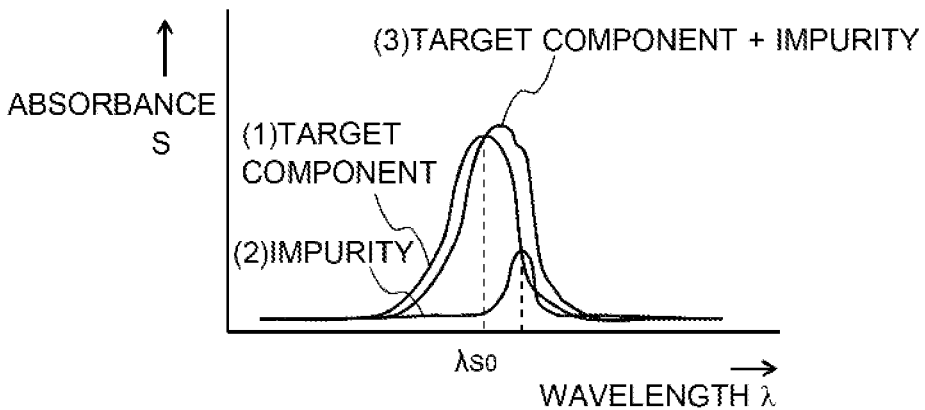
FIG. 4 is a diagram showing one example of the absorbance spectra of a target component and an impurity.

FIG. 4 is a model diagram showing a pattern of the absorbance spectrum of a target component ((1) in FIG. 4) and that of an impurity ((2) in FIG. 4) at a certain point in time in a chromatographic analysis. As shown, when the range of absorption wavelengths of the target component overlaps that of an impurity, the pattern of the absorbance spectrum actually obtained at time $T_u$ equals the sum of the pattern of the absorbance spectrum of the target component and that of the impurity ((3) in FIG. 4). As a result, a discrepancy occurs between the position of the maximum (or minimum) of the absorbance spectrum and the maximum (or minimum) absorption wavelength $\lambda_{S0}$ of the target component.

Figure 3:
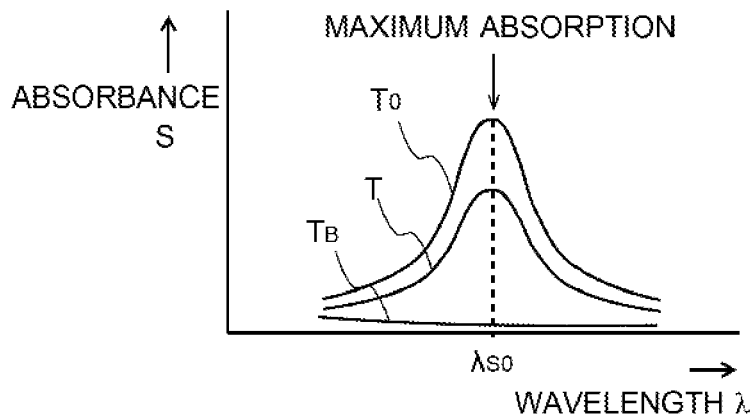
FIG. 3 is a diagram showing one example of the absorbance spectra at different measurement points.

When the target peak originates from only the target component, the maximum (or minimum) absorption wavelength $\lambda_{S0}$ of the target component coincides with the position of the maximum (or minimum) of the absorbance spectrum at any point in time within a range from the start point $T_S$ to the end point $T_E$ of the target component, as shown in FIG. 3, so that the wavelength differential coefficient at the maximum (or minimum) absorption wavelength $\lambda_{S0}$ is zero. As a result, the differential chromatogram within the time range from the start point $T_S$ to the end point $T_E$ of the target component will have a flat shape which contains only unavoidable noises, as shown by the solid line in FIG. 5. By contrast, when the target peak contains an impurity, the maximum (or minimum) absorption wavelength $\lambda_{S0}$ of the target component does not coincide with the position of the maximum (or minimum) of the absorbance spectrum at each point in time, as shown in FIG. 4, so that the wavelength differential coefficient at the maximum (or minimum) absorption wavelength $\lambda_{S0}$ takes non-zero values within the time range from $T_S$ to $T_E$. As a result, the differential chromatogram will have a non-flat shape within a time segment where the impurity is contained, as shown by the broken line in FIG. 5.

Accordingly, the determining section 26 determines whether or not the differential chromatogram is flat within the time range from the start point $T_S$ to the end point $T_E$ of the target peak (Step S8). If the differential chromatogram within that time range is flat (i.e. if the result of Step S8 in FIG. 6 is "Yes"), the determining section 26 determines that the target peak contains no impurity within the aforementioned time range, i.e. that the peak originates from only the target component (Step S9). On the other hand, if the differential chromatogram within that time range is not flat (i.e. if the result of Step S8 is "No"), the determining section 26 determines that the target peak contains an impurity within that time range (Step S10). The obtained determination result is shown to the operator through the display unit 3 (Step S11).

The determination on whether or not the differential chromatogram is flat can be made, for example, by determining whether or not a peak exists whose intensity is equal to or higher than N times the average intensity of the noise on the baseline or whose area is equal to or larger than a predetermined value. Other methods can also be used.

As described thus far, the data processing system 2 according to the first embodiment determines whether or not a target peak contains an impurity by determining whether or not the differential chromatogram is flat within the time range from the start point $T_S$ to the end point $T_E$ of the target peak on the maximum (or minimum) absorption wavelength chromatogram. Even the slightest displacement of the maximum (or minimum) absorption wavelength $\lambda_{S0}$ from the maximum (or minimum) due to the presence of an impurity will be reflected in the shape of the differential chromatogram. Thus, as compared to the conventional peak purity determination technique, the data processing system 2 according to the first embodiment can provide determination results with dramatically higher accuracies.

Furthermore, unlike the conventional technique, the data processing system 2 according to the first embodiment does not require the setting of a noise vector (which consists of noise components at respective wavelengths) as a parameter, so that the peak purity determination can be performed by a calculation process that is dramatically simpler than the conventional technique.

Another advantage of the data processing system 2 according to the first embodiment is that whether or not an impurity is contained can be more efficiently determined in a shorter period of time since the differential chromatogram is not created for the entire the measurement period but for the limited range of time from the start point $T_S$ to the end point $T_E$ of the target peak.

In the foregoing description, it was assumed that the operator selects one target peak through the operation unit 4. It is also possible to select a plurality of peaks as the target peaks. In this case, the previously described impurity-detecting process can be performed for each target peak. The system may be previously configured so that the impurity detection is performed for all the detected peaks regardless of the number of peaks detected. In this case, the process of Step S5 in the aforementioned flowchart should be omitted.

In the first embodiment, the operator is made to enter the value of the maximum (or minimum) absorption wavelength $\lambda_{S0}$ of the target component in Step S2. Another possibility is to have the operator specify the name or structural formula of the target component and order the system to retrieve a corresponding wavelength value (or values) from a database. It is also possible to provide the system with the function of automatically detecting a peak (e.g. a three-dimensional peak) from the three-dimensional chromatogram data and comparing the obtained result with a database to determine the maximum (or minimum) absorption wavelength. In this case, manual operations for the selection of the wavelength can be entirely omitted. If the target component has a plurality of maximum (or minimum) absorption wavelengths, any one of those wavelengths can be selected.

As for the setting of the time rage including the target peak, the points in time $T_S$ and $T_E$ which respectively correspond to the start and end points of the target peak may be obtained by allowing the operator to previously enter, through the operation unit 4, a time rage having an appropriate width before and after the retention time of the target peak on the wavelength chromatogram.

Another possible method is to display the wavelength chromatogram (as shown in FIG. 2) on a screen of the display unit 3 and allow the operator to visually check the chromatogram and manually specify, through the operation unit 4, two points in time which respectively correspond to the start point $T_S$ and the end point $T_E$ of the target peak.

In any of these two cases, the time range from the start point $T_S$ to the end point $T_E$ of the target peak can be set by making the operator directly enter information on that time range or perform a click function or similar operation at the positions corresponding to the start point and the end point of that time range on the wavelength chromatogram in Step S5.

In the previous description of the first embodiment, the wavelength chromatogram creator 22 created a wavelength chromatogram at the maximum (or minimum) absorption wavelength of the target component. However, the wavelength chromatogram may be created at a different wavelength in the vicinity of the maximum (or minimum) absorption wavelength of the target component. If there are a plurality of maximum (or minimum) absorption wavelengths, it is normally preferable to select the wavelength at which the strongest absorption occurs. As for the maximum (or minimum) absorption wavelength of the first component, if the presence of an impurity peak in the vicinity of the peak top of the target peak is known beforehand, and if the amount of that impurity needs to be determined, it is preferable to select a maximum (or minimum) absorption wavelength at which the differential coefficient of the absorption spectrum with respect to the wavelength has an adequately large value.

[Configuration and Operation of Chromatogram Data Processing System According to One Variation of First Embodiment]

Figure 7:
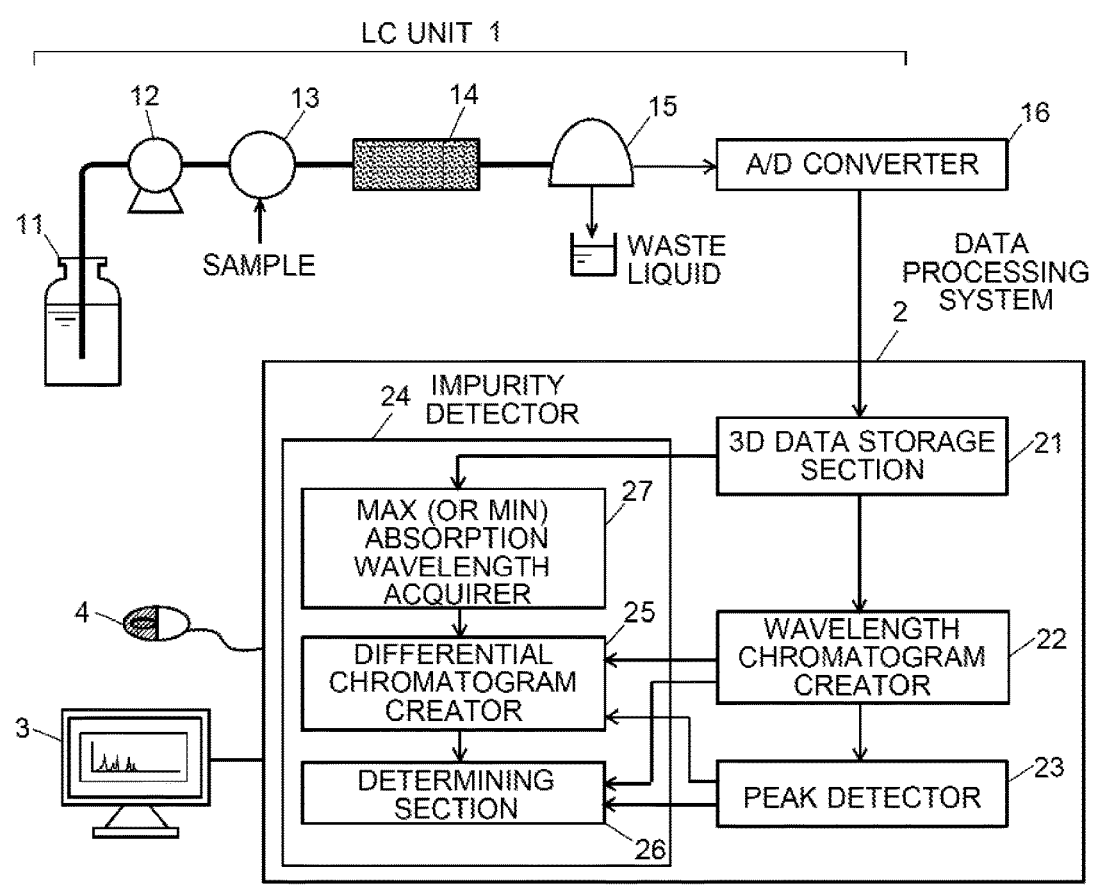
FIG. 7 is a schematic configuration diagram of a liquid chromatograph provided with a chromatogram data processing system which is another embodiment of the present invention.

A data processing system according to a variation of the first embodiment is hereinafter described with reference to FIG. 7. As shown in FIG. 7, the data processing system according to the present variation corresponds to the data processing system of the first embodiment in which a maximum (or minimum) absorption wavelength acquirer 27 is additionally provided.

The data processing system of the present variation is configured so that, if the maximum (or minimum) absorption wavelength $\lambda_{S0}$ of the target component is unknown and no database for determining that wavelength is provided, an actual measurement of a sample containing a reference specimen of the target component is performed to obtain the maximum (or minimum) absorption wavelength $\lambda_{S0}$ and use the obtained value for the processes in the subsequent stages.

Initially, a standard sample containing a reference specimen of the target component is subjected to a measurement in the LC unit 1 to obtain three-dimensional chromatogram data. The obtained three-dimensional chromatogram data are stored in the three-dimensional data storage section 21. When the operator selects an appropriate wavelength at which a peak originating from the target component is likely to appear, the wavelength chromatogram creator 22 reads an appropriate set of three-dimensional chromatogram data from the three-dimensional data storage section 21 and creates a wavelength chromatogram at the selected wavelength. The peak detector 23 detects each peak on this wavelength and finds the points in time corresponding to the start point $T_S$, the top $T_0$ and the end point $T_E$ of the peak in the same manner as described in the previous embodiment. From the detected peaks, the operator selects, through the operation unit 4, a peak originating from the reference specimen of the target component (in the present case, normally, only one peak is detected).

The maximum (or minimum) absorption wavelength acquirer 27 reads, from the three-dimensional data storage section 21, the three-dimensional chromatogram data obtained by the measurement of the standard sample containing the target component. It also obtains, from the peak detector 23, the point in time $T_0$ corresponding to the top of the peak selected by the operator. Then, the maximum (or minimum) absorption wavelength acquirer 27 calculates the wavelength differential coefficient at each wavelength on the absorbance spectrum at time $T_0$ by sequentially differentiating this absorbance spectrum with respect to the wavelength at each point on the wavelength axis.

Subsequently, the maximum (or minimum) absorption wavelength acquirer 27 finds the wavelength at which the wavelength differential coefficient becomes zero, and obtains this wavelength as the maximum (or minimum) absorption wavelength $\lambda_{S0}$ of the reference specimen of the target component. The obtained maximum (or minimum) absorption wavelength $\lambda_{S0}$ of the reference specimen is used in the peak purity determination process for a sample which will subsequently be subjected to the measurement. If a plurality of maximum (or minimum) absorption wavelengths $\lambda_{S0}$ have been acquired, the operator can select, through the operation unit 4, one wavelength which is considered to be most appropriate as the maximum (or minimum) absorption wavelength $\lambda_{S0}$. With the maximum (or minimum) absorption wavelength $\lambda_{S0}$ thus set, the peak purity determination process can be performed in the same manner as the previously described Step S3 and subsequent steps in FIG. 6.

Thus, with the data processing system according to the present variation, even if there is no information on the maximum (or minimum) absorption wavelength $\lambda_{S0}$ of the target component, a peak purity determination for the target component contained in an unknown sample can be performed if a sample containing a reference specimen of that target component is available.

[Configuration and Operation of Chromatogram Data Processing System which is Second Embodiment of Present Invention]

Figure 12:
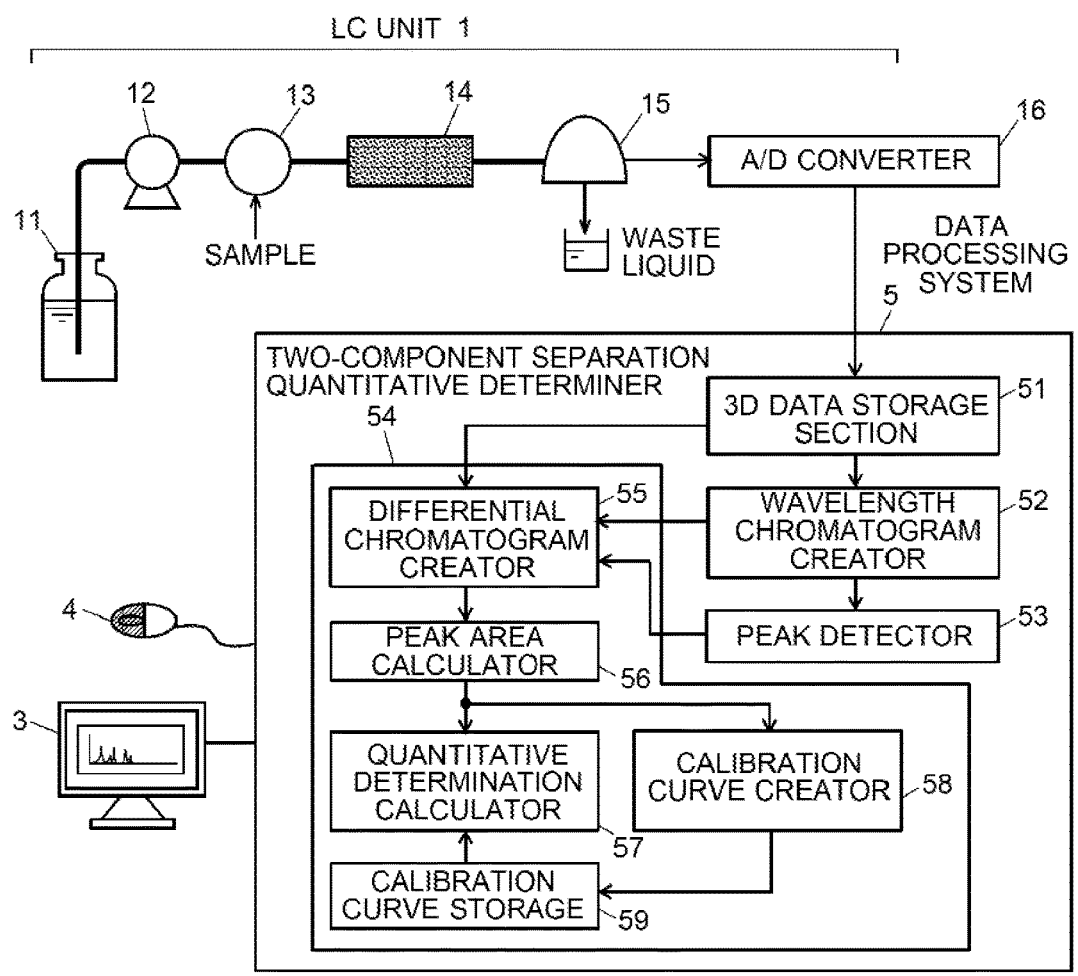
FIG. 12 is a schematic configuration diagram of a liquid chromatograph provided with a chromatogram data processing system which is still another embodiment of the present invention.

A liquid chromatograph provided with the second embodiment of the chromatograph data processing system according to the present invention is hereinafter described with reference to FIG. 12. In the system of the second embodiment, two target components x and y which cannot be sufficiently separated by the column 14 due to the closeness of their retention times can be separated by data processing based on the previously described principle, so as to separately determine their quantities. In FIG. 12, the LC unit 1 has the same configuration as the first embodiment shown in FIG. 1, and hence, will not be described.

As in the first embodiment, the data processing system 5 includes a three-dimensional data storage section 51 for storing three-dimensional chromatogram data produced by the A/D converter 16, a wavelength chromatogram creator 52 for creating, from the three-dimensional chromatogram data, a wavelength chromatogram at a specific wavelength, a peak detector 53 for detecting a peak whose quantity needs to be determined in the wavelength chromatogram and for setting a time range for that peak, as well as a two-component separation quantitative determiner 54 for separating two target components x and y selected by an operator within the set peak or time range and for determining the quantity of each target component.

The two-component separation quantitative determiner 54 includes, as its functional blocks, a differential chromatogram creator 55 for creating, for each of the two target components x and y, a differential chromatogram based on the three-dimensional chromatogram data and the maximum (or minimum) absorption wavelengths $\lambda x$ and $\lambda y$ of the target components, a peak area calculator 56 for calculating the area of a peak on the differential chromatogram, a quantitative determination calculator 57 for determining the concentration of the target component x or y by comparing the calculated area with a calibration curve (which will be described later), a calibration curve creator 58 for creating a calibration curve representing the relationship between the peak area on the differential chromatogram and the component concentration based on the results of analyses of samples containing the target components x and y at known concentrations, and a calibration curve storage section 59 for storing the created calibration curves.

A characteristic data processing operation of the liquid chromatogram system of the second embodiment is hereinafter described. In the present embodiment, for the purpose of quantitative determination of the target components x and y contained in an unknown sample at unknown concentrations, calibration curves of those components x and y are created beforehand and stored in the calibration curve storage section 59 as follows.

The operator prepares a plurality of standard samples of the target component x with different levels of concentration by diluting a reference specimen of the component x, as well as a plurality of standard samples of the target component y with different levels of concentration by diluting a reference specimen of the component y. Those standard samples are individually subjected to the measurement in the LC unit 1 to obtain three-dimensional chromatogram data. The obtained three-dimensional chromatogram data are temporarily stored in the three-dimensional data storage section 51.

The operator enters, through the operation unit 4, the values of the maximum (or minimum) absorption wavelengths $\lambda x$ and $\lambda y$ of the target components x and y. In response to this operation, the wavelength chromatogram creator 52 creates a maximum (or minimum) absorption wavelength chromatogram at each of the maximum (or minimum) absorption wavelengths $\lambda x$ and $\lambda y$, based on the entered values of the two maximum (or minimum) absorption wavelengths $\lambda x$ and $\lambda y$ as well as the three-dimensional chromatogram data obtained for each of the standard samples. The peak detector 53 detects a peak and obtains the points in time corresponding to the start point $T_S$, the top $T_O$ and the end point $T_E$ of the peak in the same manner as described in the first embodiment (in the present case, only one peak originating from either the target component x or y is detected on one maximum (or minimum) absorption wavelength chromatogram).

For a standard sample containing the component x at a certain concentration, the differential chromatogram creator 55 obtains, from the three-dimensional data storage section 51, absorbance spectra included in the time range from the start point $T_S$ to the end point $T_E$ of the peak for the component x, calculates the wavelength differential coefficient for each absorbance spectrum by differentiating the absorbance spectrum with respect to the wavelength at the maximum (or minimum) absorption wavelength $\lambda y$ of the target component y, and creates a differential chromatogram at the maximum (or minimum) absorption wavelength $\lambda y$ with the horizontal axis indicating the time and the horizontal axis indicating the calculated wavelength differential coefficient. In the present case, since the standard sample subjected to the measurement contains only the component x, the absorbance at the wavelength $\lambda x$ continuously stays at maximum (or minimum) throughout the entire range of time in which the component x is eluted. Therefore, the differential coefficient at the maximum (or minimum) absorption wavelength $\lambda x$ remains zero.

Meanwhile, although the wavelength $\lambda y$ is not the maximum (or minimum) absorption wavelength for the component x, an absorption of light by the component x also occurs at this wavelength $\lambda y$. Therefore, the wavelength differential coefficient at the maximum (or minimum) absorption wavelength $\lambda y$ of the component y changes within a range where the absorption by the component x takes place. As a result, a peak appears on the differential chromatogram at the maximum (or minimum) absorption wavelength $\lambda y$, and this peak reflects the elution profile of the component x. Accordingly, the peak area calculator 56 calculates the area value of the peak originating from the component x and appearing on the differential chromatogram at the wavelength $\lambda y$. Such a process for calculating the peak-area value originating from the component x is similarly performed for each of the differential chromatograms at the wavelength $\lambda y$ based on the three-dimensional chromatogram data obtained for the standard samples containing the component x at different concentrations.

Based on the peak-area values obtained from the differential chromatograms at the wavelength $\lambda y$ respectively created for the standard samples containing the component x at different concentrations, and based on the respective component concentrations, the calibration curve creator 58 creates a calibration curve which shows the relationship between the concentration of the component x and the peak-area value on the differential chromatogram at the wavelength $\lambda y$, and stores this curve in the calibration curve storage section 59.

Similarly, for each of the standard samples containing the component y, the differential chromatogram creator 55 creates a differential chromatogram at the maximum (or minimum) absorption wavelength $\lambda x$ of the component x based on the three-dimensional chromatogram data obtained for that sample. The peak area calculator 56 calculates the area value of the peak originating from the component y and appearing on the differential chromatogram at the wavelength $\lambda x$. Based on the peak-area values thus obtained from the differential chromatograms at the wavelength $\lambda x$ respectively created for the standard samples containing the component y at different concentrations, and based on the respective component concentrations, the calibration curve creator 58 creates a calibration curve which shows the relationship between the concentration of the component y and the peak-area value on the differential chromatogram at the wavelength $\lambda x$, and stores this curve in the calibration curve storage section 59.

Thus, the two calibration curves respectively created for the components x and y are stored in the calibration curve storage section 59.

In a quantitative measurement of the target components x and y in a sample which contains those components x and y at unknown concentrations, the measurement of the unknown sample is performed in the LC unit 1 and the thereby obtained three-dimensional data are stored in the three-dimensional data storage section 51.

Figure 15A:
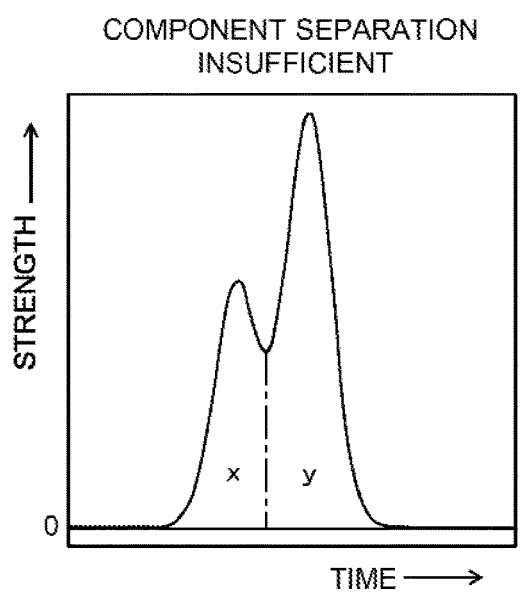
FIGS. 15A and 15B are diagrams showing examples of the chromatograms in which peaks of two components overlap each other due to insufficient peak separation.
Figure 15B:
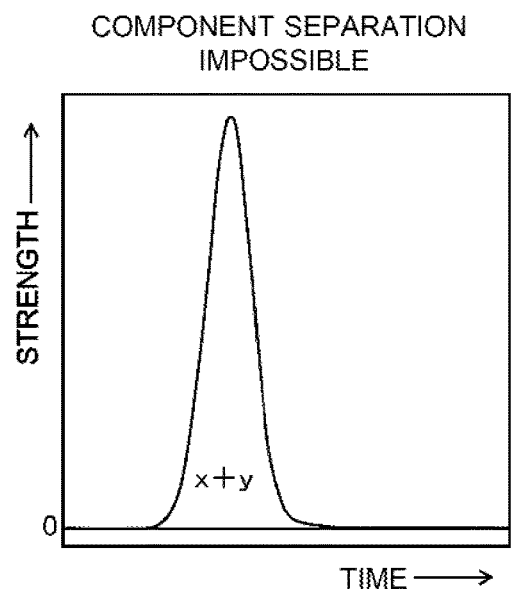

The operator enters, through the operation unit 4, the values of the maximum (or minimum) absorption wavelengths $\lambda x$ and $\lambda y$ of the target components x and y. In response to this operation, the wavelength chromatogram creator 52 reads, from the three-dimensional data storage section 51, the three-dimensional chromatogram data obtained at the two maximum (or minimum) absorption wavelengths $\lambda x$ and $\lambda y$ entered by the operator, and creates a wavelength chromatogram at each of the maximum (or minimum) absorption wavelengths $\lambda x$ and $\lambda y$. On each of the two wavelength chromatograms, the peak detector 53 detects a peak and obtains the points in time corresponding to the start point $T_S$, the top $T_0$ and the end point $T_E$ of the peak in the same manner as described in the previous embodiments. It should be noted that a peak appearing on the wavelength chromatogram may be composed of two peaks overlapping each other, as shown in FIG. 15A. To deal with a case, it is preferable, for example, to divide the composite peak into front and rear sections based on the previously given retention times of the components x and y, and to select the start point of the front section and the end point of the rear section as the start point $T_S$ and the end point $T_E$ of the entire peak, respectively.

As in the first embodiment, when a plurality of peaks have been detected in the peak detection process, information on the detected peaks can be displayed on a screen of the display unit 3 to allow the operator to select, through the operation unit 4, a target peak originating from the target component out of the displayed peaks.

Next, the differential chromatogram creator 55 retrieves, from the three-dimensional data storage section 51, absorbance spectra included in the time range from the start point to the end point of the peak detected by the peak detector 53 or selected by the operator, calculates the wavelength differential coefficient for each absorbance spectrum by differentiating the absorbance spectrum with respect to the wavelength at the maximum (or minimum) absorption wavelength $\lambda x$ of the target component x as well as at the maximum (or minimum) absorption wavelength $\lambda y$ of the target component y, and creates a differential chromatogram at each of the maximum (or minimum) absorption wavelengths $\lambda x$ and $\lambda y$. As described earlier, the influence of the absorption by the target component x does not appear on the differential chromatogram at the wavelength $\lambda x$; the peak which is observed on this chromatogram reflects the elution profile of the component y. Similarly, the influence of the absorption by the target component y does not appear on the differential chromatogram at the wavelength $\lambda y$; the peak which is observed on this chromatogram reflects the elution profile of the component x. Accordingly, the peak area calculator 56 calculates the area value of the peak appearing on each of the differential chromatograms.

The quantitative determination calculator 57 calculates the concentration value of the component y by comparing the peak-area value obtained from the differential chromatogram at the wavelength $\lambda x$ with the calibration curve for the component y read from the calibration curve storage section 59. It also calculates the concentration value of the component x by comparing the peak-area value obtained from the differential chromatogram at the wavelength $\lambda y$ with the calibration curve for the component x which is also read from the calibration curve storage section 59. The obtained results of the quantitative determination of the two target components x and y are shown to the operator through the display unit 3.

As described thus far, in the data processing system 5 according to the second embodiment, even if the target component and another (second) component are superposed on each other in an eluate, the influence of the second component can be excluded from the quantitative determination of the target component by using the area value of the peak appearing on the differential chromatogram at the maximum (or minimum) absorption wavelength of the second component. The peak appearing on this differential chromatogram reflects the elution profile of only the target component. Therefore, the present technique provides a quantitative determination result with dramatically higher accuracies than the conventional technique in which overlapping peaks are vertically divided to determine their quantities.

The variations described in the first embodiment can also be applicable in the second embodiment. For example, in addition to allowing the operator to enter the values of the maximum (or minimum) absorption wavelengths $\lambda x$ and $\lambda y$ of the target components x and y, it is possible to have the operator specify the names or structural formulas of the target components and order the system to retrieve corresponding wavelength values from a database. This method is particularly convenient in the case of using retention times in the peak detection process since using a database enables automatic retrieval of their retention times of desired components together with the wavelength values.

The present invention is not limited to the first and second embodiments. Any change, addition or modification appropriately made within the scope of the present invention will evidently fall within the scope of claims of the present patent application.

For example, the detector used in the chromatograph for acquiring three-dimensional chromatogram data to be processed by the data processing system according to the present invention does not need to be a multichannel detector (e.g. a PDA detector). Any type of detector can be used as long as it can produce an absorbance spectrum which has a comparatively broad (moderately changing) waveform so that the differential coefficient obtained by sequentially differentiating the absorbance spectrum with respect to the wavelength at each point on the wavelength axis will correctly reflect the slope of the spectrum curve at that point. However, it is inappropriate to use a detector which requires an excessive amount of time to measure absorbance over a predetermined range of wavelengths. From this viewpoint, it is preferable to use a spectrophotometer capable of high-speed wavelength scan (e.g. an ultraviolet-visible spectrophotometer, infrared spectrophotometer, near-infrared spectrophotometer or fluorescence spectrophotometer).

The chromatograph may be a gas chromatograph instead of the liquid chromatograph, although it is normally a liquid chromatograph that uses the aforementioned types of detectors. Furthermore, as already explained, the present invention can evidently be applied in a system or method for processing the data obtained by detecting a component in a sample which has been introduced by the FIA method without being separated into components, instead of the data obtained by detecting a sample which has passed through a column of a chromatograph.

EXPLANATION OF NUMERALS

1 . . . LC Unit
11 . . . Mobile-Phase Container
12 . . . Liquid-Sending Pump
13 . . . Sample Injection Unit
14 . . . Column
15 . . . PDA Detector
16 . . . A/D Converter
2, 5 . . . Data Processing System
21, 51 . . . Three-Dimensional Data Storage Section
22, 52 . . . Wavelength Chromatogram Creator 23, 53 . . . Peak Detector
24 . . . Impurity Detector
25 . . . Differential Chromatogram Creator
26 . . . Determining Section
27 . . . Maximum (or Minimum) Absorption Wavelength Acquirer
3 . . . Display Unit
4 . . . Operation Unit
54 . . . Two-Component Separation Quantitative Determiner
55 . . . Differential Chromatogram Creator
56 . . . Peak Area Calculator
57 . . . Quantitative Determination Calculator
58 . . . Calibration Curve Creator
59 . . . Calibration Curve Storage Section

The invention claimed is:

1. A three-dimensional chromatograph system, comprising:
   a three-dimensional chromatograph that temporally separates components contained in a target sample, the separated components including a first component and a second component;
   a detector that detects the separated components; and
   a data processing system that is implemented by a computer and produces three-dimensional chromatogram data with respect to time, wavelength, and absorbance acquired with the three-dimensional chromatograph based on the detected separated components, the data processing system including,
   a) a differential chromatogram creator for performing data processing, based on the three-dimensional chromatogram data, in such a manner that, for each of absorbance spectra showing a relationship between the wavelength and the absorbance at respective points in time within an entire or predetermined time range, a wavelength differential coefficient which is a differential coefficient of an absorbance spectrum at a maximum or minimum absorption wavelength of the first component is calculated; and
   b) a chromatogram waveform processor for performing, based on the wavelength differential coefficient, either a process of determining whether or not a peak of the second component overlaps a peak of the first component whereby analysis of the overlapping peaks is improved, or a process of determining a quantity of the second component overlapping the peak of the first component whereby determining whether or not an impurity is contained in the peak of the first component, which is the target component, is improved.

2. The three-dimensional chromatograph system according to claim 1, wherein the data processing system further comprises:
   c) a wavelength chromatogram creator for creating, based on the three-dimensional chromatogram data, a wavelength chromatogram showing a relationship between the time and the absorbance for an absorption wavelength of the first component,
   wherein:
   the differential chromatogram creator performs data processing, based on the three-dimensional chromatogram data, in such a manner that, for each of absorbance spectra obtained at respective points in time within a time range including a peak of a target component on the wavelength chromatogram, the wavelength differential coefficient at the maximum or minimum absorption wavelength of the first component is calculated so as to create a differential chromatogram showing a temporal change of the wavelength differential coefficient.

3. The three-dimensional chromatograph system for processing three-dimensional chromatogram data according to claim 2, wherein:
   the chromatogram waveform processor determines whether or not an impurity is contained in the peak of the target component by determining whether or not the differential chromatogram is flat.

4. The three-dimensional chromatograph system according to claim 2, wherein the data processing system further comprises:
   d) a peak detector for detecting a peak on the wavelength chromatogram and for determining a start point and an end point of the peak,
   wherein the differential chromatogram creator creates a differential chromatogram within a time range from the start point to the end point of the peak of the target component on the wavelength chromatogram.

5. The three-dimensional chromatograph system according to claim 2, wherein the data processing system further comprises:
   e) a maximum absorption wavelength acquirer or a minimum absorption wavelength acquirer for calculating the maximum or minimum absorption wavelength of a known target component by differentiating, with respect to the wavelength, an absorption spectrum at a point in time corresponding to a top of the peak on the wavelength chromatogram based on three-dimensional chromatogram data obtained for a sample containing the known target component.

6. The three-dimensional chromatograph system according to claim 1, wherein:
   the differential chromatogram creator performs data processing, based on the three-dimensional chromatogram data, in such a manner that, for each of the absorbance spectra obtained at respective points in time within the entire or predetermined time range, the wavelength differential coefficient at the maximum or minimum absorption wavelength of the first component which is a first target component is calculated so as to create a first differential chromatogram showing a temporal change of the wavelength differential coefficient, and the wavelength differential coefficient at the maximum or minimum absorption wavelength of the second component which is a second target component is calculated so as to create a second differential chromatogram showing a temporal change of the wavelength differential coefficient; and
   the chromatogram waveform processor determines a quantity of the second target component based on a peak on the first differential chromatogram at the maximum or minimum absorption wavelength of the first target component as well as a quantity of the first target component based on a peak on the second differential chromatogram at the maximum or minimum absorption wavelength of the second target component.

7. The three-dimensional chromatograph system according to claim 6, wherein the data processing system further comprises:
   a calibration information storage for storing, for each of the first and second target components, calibration information showing a relationship between an area or height of a peak appearing on the differential chromatogram and a concentration of the component;

a peak information calculator for calculating the area or height of the peak appearing on each of the first and second differential chromatograms respectively created at the maximum or minimum absorption wavelength of the first target component and the maximum or minimum absorption wavelength of the second target component based on the three-dimensional chromatogram data corresponding to the target sample; and a quantity calculator for determining the quantity of each target component by comparing the area or height of the peak calculated by the peak information calculator with the calibration information.

8. A three-dimensional chromatography method, comprising:

temporally separating components contained in a target sample using a chromatograph part, the separated components including a first component and a second component;

detecting the separated components;

producing three-dimensional chromatogram data with respect to time, wavelength and absorbance with a three-dimensional chromatograph based on the detected separated components by implementing a computer, a) performing data processing, based on the three-dimensional chromatogram data, in such a manner that, for each of absorbance spectra showing a relationship between the wavelength and the absorbance at respective points in time within an entire or predetermined time range, a wavelength differential coefficient which is a differential coefficient of an absorbance spectrum at a maximum or minimum absorption wavelength of the first component is calculated; and b) either determining whether or not a peak of the second component overlaps a peak of the first component whereby analysis of the overlapping peaks is improved, or determining a quantity of the second component overlapping the peak of the first component, based on the wavelength differential coefficient whereby determining whether or not an impurity is contained in the peak of the first component, which is the target component, is improved.

9. The method according to claim 8, further comprising:

c) creating a wavelength chromatogram showing a relationship between the time and the absorbance for an absorption wavelength of the first component based on the three-dimensional chromatogram data, wherein:

in the differential chromatogram creating, based on the three-dimensional chromatogram data, the wavelength differential coefficient at the maximum or minimum absorption wavelength of the first component is calculated for each of absorbance spectra obtained at respective points in time within a time range including a peak of a target component on the wavelength chromatogram, and a differential chromatogram showing a temporal change of the wavelength differential coefficient is created.

10. The method according to claim 8, wherein:

in the differential chromatogram creating, data processing is performed, based on the three-dimensional chromatogram data, in such a manner that, for each of the absorbance spectra obtained at respective points in time within the entire or predetermined time range, the wavelength differential coefficient at the maximum or minimum absorption wavelength of the first component which is a first target component is calculated so as to create a first differential chromatogram showing a temporal change of the wavelength differential coefficient, and the wavelength differential coefficient at the maximum or minimum absorption wavelength of the second component which is a second target component is calculated so as to create a second differential chromatogram showing a temporal change of the wavelength differential coefficient; and in the chromatogram waveform processing, a quantity of the second target component is determined based on a peak on the first differential chromatogram at the maximum or minimum absorption wavelength of the first target component, and a quantity of the first target component is determined based on a peak on the second differential chromatogram at the maximum or minimum absorption wavelength of the second target component.

* * * * *